(12) United States Patent
Burnie et al.

(10) Patent No.: US 7,785,571 B2
(45) Date of Patent: Aug. 31, 2010

(54) TREATMENT OF FUNGAL INFECTIONS

(75) Inventors: James Peter Burnie, Manchester (GB); Ruth Christine Matthews, Manchester (GB)

(73) Assignee: Neutec Pharma Limited (GB)

( * ) Notice: Subject to any disclaimer, the term of this patent is extended or adjusted under 35 U.S.C. 154(b) by 714 days.

(21) Appl. No.: 11/587,020

(22) PCT Filed: Apr. 18, 2005

(86) PCT No.: PCT/GB2005/001478

§ 371 (c)(1),
(2), (4) Date: Oct. 20, 2006

(87) PCT Pub. No.: WO2005/102386

PCT Pub. Date: Nov. 3, 2005

(65) Prior Publication Data

US 2008/0095778 A1    Apr. 24, 2008

(30) Foreign Application Priority Data

Apr. 23, 2004 (GB) ................. 0409077.5

(51) Int. Cl.
A61K 49/00 (2006.01)
A61K 39/02 (2006.01)
A61K 39/395 (2006.01)

(52) U.S. Cl. .............. 424/9.2; 424/9.1; 424/130.1; 424/139.1; 424/150.1; 424/164.1; 424/185.1; 424/234.1; 530/300; 530/350

(58) Field of Classification Search .......... 424/9.1, 424/9.2, 130.1, 133.1, 139.1, 150.1, 164.1, 424/184.1, 185.1, 234.1; 530/300, 350
See application file for complete search history.

(56) References Cited

U.S. PATENT DOCUMENTS 5,952,300 A    9/1999  Nerurkar et al. ............ 514/11

FOREIGN PATENT DOCUMENTS

WO    WO 01/76627       10/2001
WO    WO 2004/026303     4/2004

*Primary Examiner*—Rodney P. Swartz
(74) *Attorney, Agent, or Firm*—Baker & Hostetler LLP

(57) ABSTRACT

A composition comprising an antibody or an antigen binding fragment thereof specific for at least one epitope of hsp90 from an organism of the *Aspergillus* genus, and at least one antifungal agent selected from the group consisting of: itraconazole and voriconazole.

27 Claims, No Drawings

SEQUENCE LISTING

```
<160> NUMBER OF SEQ ID NOS: 3

<210> SEQ ID NO 1
<211> LENGTH: 12
<212> TYPE: PRT
<213> ORGANISM: Candida sp.

<400> SEQUENCE: 1

Asn Lys Ile Leu Lys Val Ile Arg Lys Asn Ile Val
1               5                   10

<210> SEQ ID NO 2
<211> LENGTH: 6
<212> TYPE: PRT
<213> ORGANISM: Aspergillus sp.

<400> SEQUENCE: 2

Lys Ile Met Lys Val Ile
1               5
```

```
<210> SEQ ID NO 3
<211> LENGTH: 248
<212> TYPE: PRT
<213> ORGANISM: Artificial Sequence
<220> FEATURE:
<223> OTHER INFORMATION: Synthetically generated peptide

<400> SEQUENCE: 3

His Met Ala Glu Val Gln Leu Val Glu Ser Gly Ala Glu Val Lys Lys
1               5                  10                  15

Pro Gly Glu Ser Leu Arg Ile Ser Cys Lys Gly Ser Gly Cys Ile Ile
            20                  25                  30

Ser Ser Tyr Trp Ile Ser Trp Val Arg Gln Met Pro Gly Lys Gly Leu
        35                  40                  45

Glu Trp Met Gly Lys Ile Asp Pro Gly Asp Ser Tyr Ile Asn Tyr Ser
    50                  55                  60

Pro Ser Phe Gln Gly His Val Thr Ile Ser Ala Asp Lys Ser Ile Asn
65                  70                  75                  80

Thr Ala Tyr Leu Gln Trp Asn Ser Leu Lys Ala Ser Asp Thr Ala Met
                85                  90                  95

Tyr Tyr Cys Ala Arg Gly Gly Arg Asp Phe Gly Asp Ser Phe Asp Tyr
            100                 105                 110

Trp Gly Gln Gly Thr Leu Val Thr Val Ser Ser Gly Gly Gly Gly Ser
            115                 120                 125

Gly Gly Gly Gly Ser Gly Gly Gly Gly Ser Asp Val Val Met Thr Gln
            130                 135                 140

Ser Pro Ser Phe Leu Ser Ala Phe Val Gly Asp Arg Ile Thr Ile Thr
145                 150                 155                 160

Cys Arg Ala Ser Ser Gly Ile Ser Arg Tyr Leu Ala Trp Tyr Gln Gln
                165                 170                 175

Ala Pro Gly Lys Ala Pro Lys Leu Leu Ile Tyr Ala Ala Ser Thr Leu
            180                 185                 190

Gln Thr Gly Val Pro Ser Arg Phe Ser Gly Ser Gly Ser Gly Thr Glu
            195                 200                 205

Phe Thr Leu Thr Ile Asn Ser Leu Gln Pro Glu Asp Phe Ala Thr Tyr
        210                 215                 220

Tyr Cys Gln His Leu Asn Ser Tyr Pro Leu Thr Phe Gly Gly Gly Thr
225                 230                 235                 240

Lys Val Asp Ile Lys Arg Ala Ala
                245
```

TREATMENT OF FUNGAL INFECTIONS

CROSS-REFERENCE TO RELATED APPLICATIONS

This application is the National Stage of International Application No. PCT/GB2005/001478, filed on Apr. 18, 2005, which claims the benefit of United Kingdom Patent Application No. 0409077.5, filed on Apr. 23, 2004. The contents of both of those applications is incorporated herein by reference in their entireties.

The present invention relates to novel compositions and preparations comprising effective antifungal agents together with an antibody which can be incorporated into the compositions and preparations.

Fungal infections are a major cause of patient mortality in the intensive care unit and more generally in immunocompromised and debilitated patients (Gold, J. W. M., 1984, Am. J. Med. 76: 458-463; Klein, R. S. et al., 1984, N. Engl. J. Med. 311: 354-357; Burnie, J. P., 1997, Current Anaesthesia & Critical Care 8: 180-183). The presence and persistence of fungal infections can be attributed to the selective pressure of broad-spectrum antifungals, frequently prolonged stay of patients in facilities such as an intensive care unit, problems in diagnosing the infections, and the lack of efficacy of the fungal agents used in therapy. While strict hygienic control may result in some prevention of fungal infections in a hospital or other environment, outbreaks of infections remain a serious problem and need to be addressed.

Although the majority of clinical manifestations of mycoses are caused predominantly by *Aspergillus fumigatus*, other *Aspergillus* species such as *A. flavus, A. terreus*, and *A. niger* are also associated with severe infections in the immunocompromised host (Espinel-Ingroff, A., 2003, J. Clin. Microbiol. 41: 403-409).

Detection and diagnosis of the fungal pathogen responsible for an infection is critical for subsequent therapy because antifungal agents may be more effective against certain strains. GB2240979 and EP0406029 (herein incorporated by reference in their entirety) disclosed a fungal stress protein and antibody thereto which could be used in a sensitive and highly specific test for detection of fungal pathogens.

Traditionally, fungal infections caused by *Aspergillus* and *Candida* species have been treated by the antifungal agent amphotericin B, regarded as the "gold standard" of systemic antifungal therapy (Burnie, J. P., 1997, supra). Unfortunately, amphotericin B is itself highly toxic and its use is tempered by side effects including chills, fever, myalgia or thrombophlebitis. Other antifungal agents include the oral azole drugs (miconazole, ketoconazole, itraconazole, fluconazole, voriconazole) and 5-fluorocytosine. However, many fungal species are becoming resistant to antifungal agents such as fluconazole, and these species often occur in patients where this drug has been administered prophylactically. In response to the increasing prevalence of antifungal resistant strains and despite the recent advances made in therapeutic drugs such as fluconazole, itraconazole and systemic liposomal-based variants of amphotericin B (Burnie, J. P., 1997, supra), the need for effective agents for treatment of fungal infections remains acute.

The above-identified need was addressed in WO 01/76627, which discloses a composition for the treatment of human or animal fungal infections. The composition comprises an antibody specific for a conserved epitope of the fungal stress protein, hsp90, the antibody being combined with the known polyene antifungal agents, particularly amphotericin B. Specifically, the antibody (hereinafter referred to as Mycograb® recognises the epitope being displayed by the peptide having the sequence of SEQ ID NO: 1, which is conserved throughout many fungal species. Surprisingly, it was shown that the efficacy of amphotericin B against a wide variety of pathologically important fungal strains (e.g. *Candida* species) was significantly enhanced in the presence of the antibody, thereby allowing for either lower treatment dosages or more effective treatment at the same dose, which allowed for reduction of unwanted side-effects. Furthermore, the composition disclosed in WO 01/76627 allows for effective treatment of fungal infections which were inherently resistant to the fungal agent used in the composition.

Importantly, fluconazole (an oral azole antifungal agent) in combination with Mycograb® antibody was shown to have little synergy against *Candida* strains.

All of the azole antifungal agents operate via a common mode of action, by preventing the synthesis of ergosterol, the major sterol component of fungal plasma membranes, through inhibition of the fungal cytochrome P450-dependent enzyme lanosterol 14-α-demethylase. The resulting depletion of ergosterol and the concomitant accumulation of 14-α-methylated precursors interferes with the bulk function of ergosterol in fungal membranes and alters both the fluidity of the membrane and the activity of several membrane-bound enzymes. The net effect is an inhibition of fungal growth and replication (Maertens, J. A., 2004, Clin. Microbiol. Infect. 10 (Suppl. 1): 1-10).

Since fluconazole in combination with Mycograb® antibody exhibited little synergy against *Candida* strains, and the mode of action of oral azole antifungal agents is common, it was logical that other oral azole antifungal agents such as miconazole, ketoconazole, itraconazole, and voriconazole would also display no synergy in combination with Mycograb® antibody.

The present inventors have now found that despite the prior finding that azole antifungal agents displayed little or no synergy with the Mycograb® antibody disclosed in WO 01/76627 in the treatment of infections due to *Aspergillus* or *Candida* strains, there is a therapeutic synergy between the oral azole antifungal agents itraconazole, and voriconazole, in combination with Mycograb® antibody. Experiments (below) have shown that this synergy is so far limited to itraconazole and voriconazole, although it is possible that other oral azole antifungal agents which have not yet been tested, or are in development may also show some synergy with Mycograb® antibody.

According to the present invention there is provided a composition comprising an antibody or an antigen binding fragment thereof specific for at least one epitope of hsp90 from an organism of the *Aspergillus* genus, and at least one antifungal agent selected from the group consisting of: itraconazole and voriconazole.

Further provided is a combined preparation, e.g. a pharmaceutical pack, comprising an antibody or an antigen binding fragment thereof specific for at least one epitope of hsp90 from an organism of the *Aspergillus* genus, and at least one antifungal agent selected from the group consisting of: itraconazole and voriconazole, for simultaneous, separate or sequential use in the treatment of fungal infections.

Further provided is a method of manufacture of a medicament for the treatment of fungal infections of the human or animal body characterized in the use of an antibody or an antigen binding fragment thereof specific for at least one epitope of hsp90 from an organism of the *Aspergillus* genus, and at least one antifungal agent selected from the group consisting of: itraconazole and voriconazole.

Further provided is the use of a composition comprising an antibody or an antigen binding fragment thereof specific for at least one epitope of hsp90 from an organism of the *Aspergillus* genus, and an antifungal agent comprising at least one antifungal agent selected from the group consisting of: itraconazole and voriconazole, in a method of manufacture of a medicament for the treatment of fungal infections.

Preliminary results also indicate that posaconazole is capable of achieving similar synergistic results and so the present invention also extends to compositions, combined preparations, methods of manufacture and uses of posaconazole and an antibody or an antigen binding fragment thereof specific for at least one epitope of hsp90 from an organism of the *Aspergillus* genus.

The antibody or antigen binding fragment thereof may be specific for the epitope displayed by a peptide comprising the sequence of SEQ ID NO: 1.

The antibody or antigen binding fragment thereof may be specific for the epitope displayed by a peptide comprising the sequence of SEQ ID NO: 2.

Antibodies, their manufacture and uses are well known and disclosed in, for example, Harlow, E. and Lane, D., Antibodies: A Laboratory Manual, Cold Spring Harbor Laboratory Press, Cold Spring Harbor, N.Y., 1999.

The antibodies may be generated using standard methods known in the art. Examples of antibodies include (but are not limited to) polyclonal, monoclonal, chimeric, single chain, Fab fragments, fragments produced by a Fab expression library, and antigen binding fragments of antibodies.

Antibodies may be produced in a range of hosts, for example goats, rabbits, rats, mice, humans, and others. They may be immunized by injection with fungal stress proteins, or any fragment or oligopeptide thereof which has immunogenic properties. Depending on the host species, various adjuvants may be used to increase an immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (Bacille Calmette-Guerin) and *Corynebacterium parvum* are particularly useful.

Monoclonal antibodies to fungal stress proteins, or any fragment or oligopeptide thereof may be prepared using any technique which provides for the production of antibody molecules by continuous cell lines in culture. These include, but are not limited to, the hybridoma technique, the human B-cell hybridoma technique, and the EBV-hybridoma technique (Koehler et al., 1975, Nature, 256: 495-497; Kosbor et al., 1983, Immunol. Today 4: 72; Cote et al., 1983, PNAS USA, 80: 2026-2030; Cole et al., 1985, Monoclonal Antibodies and Cancer Therapy, Alan R. Liss Inc., New York, pp. 77-96).

In addition, techniques developed for the production of "chimeric antibodies", the splicing of mouse antibody genes to human antibody genes to obtain a molecule with appropriate antigen specificity and biological activity can be used (Morrison et al., 1984, PNAS USA, 81: 6851-6855; Neuberger et al., 1984, Nature, 312: 604-608; Takeda et al., 1985, Nature, 314: 452-454). Alternatively, techniques described for the production of single chain antibodies may be adapted, using methods known in the art, to produce fungal stress protein-specific single chain antibodies. Antibodies with related specificity, but of distinct idiotypic composition, may be generated by chain shuffling from random combinatorial immunoglobin libraries (Burton, D. R., 1991, PNAS USA, 88: 11120-11123).

Antibodies may also be produced by inducing in vivo production in the lymphocyte population or by screening recombinant immunoglobulin libraries or panels of highly specific binding reagents (Orlandi et al., 1989, PNAS USA, 86: 3833-3837; Winter, G. et al., 1991, Nature, 349: 293-299).

Antigen binding fragments may also be generated, for example the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al., 1989, Science, 256: 1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between the fungal stress protein or any fragment or oligopeptide thereof, and its specific antibody. A two-site, monoclonal-based immunoassay utilizing monoclonal antibodies specific to two non-interfering fungal stress protein epitopes may be used, but a competitive binding assay may also be employed (Maddox et al., 1983, J. Exp. Med., 158: 1211-1216).

For example, the antibody used in the composition or combined preparation may comprise the sequence of SEQ ID NO: 3.

The composition or the combined preparation may be used in the treatment of fungal infections. The fungal infection may be due to an organism of the *Aspergillus* genus.

The fungal infection may be resistant to said antifungal agent per se.

The composition or the combined preparation may be used in a method of treatment of fungal infections of the human or animal body.

The composition or preparation may additionally comprise a pharmaceutically acceptable carrier, diluent or excipient. Similarly, any method of manufacture of the present invention or use in same may also comprise the use of a pharmaceutically acceptable carrier, diluent or excipient. Examples of pharmaceutically acceptable carriers, diluents and excipients are well known in the art, for example see: Remington's Pharmaceutical Sciences and US Pharmacopoeia, (1984, Mack Publishing Company, Easton, Pa., USA).

Further provided is a method of treatment of fungal infections of the human or animal body comprising administering a therapeutically effective quantity of an antibody or an antigen binding fragment thereof specific for at least one epitope of hsp90 from an organism of the *Aspergillus* genus, and at least one antifungal agent selected from the group consisting of: itraconazole and voriconazole, to a patient in need of same.

The composition or combined preparation may be administered orally.

Further provided is a kit comprising an antibody or an antigen binding fragment thereof specific for at least one epitope of hsp90 from an organism of the *Aspergillus* genus, and at least one antifungal agent selected from the group consisting of: itraconazole and voriconazole.

The kit may be for use in the treatment of fungal infections.

The antibody or antigen binding fragment thereof according to the present invention may be labelled with a detectable label or may be conjugated with an effector molecule, for example a drug e.g. an anti-fungal agent such as itraconazole or voriconazole, or a toxin, such as ricin, or an enzyme, using conventional procedures, and the invention extends to such labelled antibodies or antibody conjugates.

If desired, mixtures of antibodies may be used for diagnosis or treatment, for example mixtures of two or more antibodies recognizing different epitopes of a fungal stress protein according to the invention, and/or mixtures of antibodies of a different class, e.g. mixtures of IgG and IgM antibodies recognizing the same or different epitope(s) of the invention.

The contents of each of the references discussed herein, including the references cited therein, are herein incorporated by reference in their entirety.

The present invention will be further apparent from the following description, which shows, by way of example only, specific embodiments of the composition and experimentation therewith.

Experiments described below investigated the antifungal effect of Mycograb® antibody used in combination with the antifungals agents amphotericin B, caspofungin, voriconazole and itraconazole. Mycograb® antibody recognizes the epitopes displayed by the peptides having the sequence of SEQ ID NOs: 1 and 2. Results show that a surprisingly strong synergistic effect is demonstrated for voriconazole and itraconazole in combination with Mycograb® antibody against a variety of clinically important *Aspergillus* species. This synergistic effect has significant implications for clinical treatment of fungal infections.

Materials and Methods

Antifungal Agents

Stock solutions of amphotericin B (AMB, Sigma), caspofungin (Caspo), voriconazole (VOR) and itraconazole (ITZ) were prepared according to the National Committee for Clinical Laboratory Standards (M38-A) in RPMI 1640 with glutamine broth medium, buffered to pH 7.0 with 0.165 mmol/liter morpholinopropanesulphonic acid (MOPS). AMB stock solutions were prepared as a 100× series in 100% dimethyl sulfoxide (DMSO) and diluted in medium to a concentration range of 0.03125 to 16 μg/ml. Caspofungin, voriconazole and itraconazole were tested at a concentration range of 0.03125 to 1024 μg/ml, and Mycograb® (NeuTec Pharma plc) at a concentration range of 0.25 to 1024 μg/ml.

Test Isolates

Clinical isolates of *Aspergillus fumigatus* (2), *A. flavus* (1), *A. terreus* (1) and *A. niger* (1) were obtained from the Department on Microbiology, Manchester Royal Infirmary, Manchester, UK.

Antibody

The DNA sequence of the Mycograb® antibody which is specific for a fungal hsp90 stress protein epitope having the sequence of SEQ ID NO: 1 (as disclosed in GB2240979 and EP0406029) was genetically modified by codon optimisation optimization for expression in *Escherichia coli* (Operon Technologies Inc., Alameda, Calif., USA) and inserted into an *E. coli* expression vector. The amino acid sequence of the Mycograb® of the present invention comprises the sequence of SEQ ID NO: 3 (includes the heavy, light and spacer domains).

Mycograb® antibody was expressed in an *Escherichia coli* host and purified by affinity chromatography using an imidazole exchange column using standard molecular biology protocols (see, for example, Harlow & Lane, supra; Sambrook, J. et al., 1989, Molecular Cloning: A Laboratory Manual, 2nd Edition, Cold Spring Harbor Laboratory Press, Cold Spring Harbor, N.Y.; Sambrook, J. & Russell, D., 2001, Molecular Cloning: A Laboratory Manual, 3rd Edition, Cold Spring Harbor Laboratory Press, Cold Spring Harbor). Mycograb® antibody was isolated up to 95% purity.

Formulations of Mycograb® antibody were prepared as follows: a vial containing 10 mg of pure Mycograb® antibody, 150 mg of pharmaceutical grade (Ph Eur) Urea and 174 mg L-Arginine (Ph Eur) were reconstituted in 5 ml water.

Cross-Reactivity of Mycograb® Antibody with *Aspergillus* sp. hsp90

Immunoblotting has previously been used to dissect the antibody response to *Aspergillus fumigatus* in patients with allergic bronchopulmonary aspergillosis, aspergilloma, and invasive aspergillosis. This identified multiple antigens of molecular weight varying from 18-92 kDa. One antigen at 88 kDa was identified as an hsp90 homolog based on its cross-reaction with Mycograb® antibody (Burnie, J. P., and R. C. Matthews. 1991. J. Clin. Microbiol. 29:2099-106). Epitope mapping has revealed that Mycograb® antibody is reactive toward the epitope displayed by the peptide having the sequence of SEQ ID NO: 2, which is conserved in both *A. fumigatus* and *A. niger*.

Antifungal Susceptibility Testing

The minimal inhibitory concentrations (MICs) of amphotericin B, caspofungin, voriconazole and itraconazole, and Mycograb® antibody were determined by broth microdilution according to the National Committee for Clinical Laboratory Standards document M38-A. In brief, AMB (0.03125 to 16 μg/ml), caspofungin, voriconazole and itraconazole (0.03125 to 1024 μg/ml) and Mycograb® (0.25 to 1024 μg/ml) concentrations were tested alone and in combination by MIC endpoints and checkerboard titrations. An inoculum suspension was prepared in buffered RPMI with glutamine medium by probing colonies from a 7 day old Sabouraud plate. The suspension was adjusted to 0.09-0.11 (80% to 82% transmittance) for *Aspergillus* species, 0.15-0.17 (68% to 70% transmittance). The inoculum was diluted a further 1:2 when added to the antifungal agents in the assay (final inoculum ($0.4 \times 10^4$ to $0.5 \times 10^4$). For AMB and Mycograb®, either alone or in combination, the endpoint was determined as the concentration to produce no growth (MIC-0). Microtiter plates were incubated at 37° C. without agitation for 48 hours for *Aspergillus* species. For caspofungin, voriconazole and itraconazole, either alone or in combination with Mycograb® antibody, the MIC endpoint was determined as the concentration resulting in a prominent decrease in turbidity ($\geq 50\%$ growth inhibition, MIC-2) compared to the growth control (Keele D J et al. Diagn Microbial Infect Dis 2001 November; 41(3):121-6, Evaluation of Amphotericin B and Flucytosine in Combination Against *Candida albicans* and *Cryptococcus neoformans* Using Time-Kill Methodology; Espinel-Ingroff, A., 2003, J. Clin. Microbiol. 41: 403-409). The final inhibitory concentration (FIC) was calculated for each drug by dividing the MIC in the presence of the second drug by the MIC in its absence. For each combination, two fractions were produced which were summated to produce the fractional final inhibitory concentration. Synergy was defined by value of $\leq 0.5$, indifference was defined by a value of $>0.5$ to $<4.0$, and antagonism was defined by a value of $\geq 4.0$ (Matthews et al., 2003).

Results

Mycograb® antibody, in addition to recognizing the epitope displayed by the peptide having the sequence of SEQ ID NO: 1, also recognizes the conserved *Aspergillus* species epitope displayed by the peptide having the sequence of SEQ ID NO: 2.

In vitro experiments examining the effect of combining an Mycograb® antibody and antifungal agents are presented in Tables 1-4.

TABLE 1

Checkerboard assay of amphotericin B and Mycograb (RTM) antibody against *Aspergillus* species

| Strain | Agent | MIC-0 (μg/ml) of each agent Alone | Combination | FIC (μg/ml) | FICI | Outcome |
|---|---|---|---|---|---|---|
| *A. fumigatus* | AMB | 2 | 1 | 0.5 | 0.5 | Indifferent |
| | Mycograb | 512 | 4 | 0.01 | | |
| *A. fumigatus* C12 | AMB | 2 | 1 | 0.5 | 0.531 | Indifferent |
| | Mycograb | 512 | 16 | 0.031 | | |
| *A. niger* | AMB | 2 | 1 | 0.5 | 0.5 | Indifferent |
| | Mycograb | 512 | 4 | 0.01 | | |
| *A. flavus* | AMB | 4 | 4 | 1 | 2 | Indifferent |
| | Mycograb | 512 | 512 | 1 | | |
| *A. terreus* | AMB | 4 | 4 | 1 | 2 | Indifferent |
| | Mycograb | 512 | 512 | 1 | | |

TABLE 2

Checkerboard assay of caspofungin and Mycograb (RTM) antibody against *Aspergillus* species

| Strain | Agent | MIC-2 (μg/ml) of each agent Alone | Combination | FIC (μg/ml) | FICI | Outcome |
|---|---|---|---|---|---|---|
| *A. fumigatus* | Caspo | 0.125 | 0.0625 | 0.5 | 0.562 | Indifferent |
| | Mycograb | 1024 | 32 | 0.062 | | |
| *A. fumigatus* C12 | Caspo | 0.125 | 0.0625 | 0.5 | 0.562 | Indifferent |
| | Mycograb | 1024 | 16 | 0.062 | | |
| *A. niger* | Caspo | 1 | 0.125 | 0.125 | 0.125 | Synergy |
| | Mycograb | 256 | 0.0625 | 0.0001 | | |
| *A. flavus* | Caspo | 1 | 0.5 | 0.5 | 0.500 | Indifferent |
| | Mycograb | 512 | 0.0625 | 0.0001 | | |
| *A. terreus* | Caspo | 0.3125 | 0.078 | 0.25 | 0.312 | Synergy |
| | Mycograb | 1024 | 32 | 0.031 | | |

TABLE 3

Checkerboard assay of itraconazole and Mycograb (RIM) antibody against *Aspergillus* species

| Strain | Agent | MIC-2 (μg/ml) of each agent Alone | Combination | FIC (μg/ml) | FICI | Outcome |
|---|---|---|---|---|---|---|
| *A. fumigatus* | ITZ | 0.5 | 0.0312 | 0.0625 | 0.0781 | Synergy |
| | Mycograb | 1024 | 16 | 0.016 | | |
| *A. fumigatus* C12 | ITZ | 0.5 | 0.125 | 0.25 | 0.2578 | Synergy |
| | Mycograb | 1024 | 8 | 0.008 | | |
| *A. niger* | ITZ | 0.125 | 0.0156 | 0.125 | 0.375 | Synergy |
| | Mycograb | 16 | 4 | 0.25 | | |
| *A. flavus* | ITZ | 0.125 | 0.0312 | 0.25 | 0.25 | Synergy |
| | Mycograb | 512 | 0.25 | 0.0005 | | |
| *A. terreus* | ITZ | 0.125 | 0.0312 | 0.25 | 0.281 | Synergy |
| | Mycograb | 1024 | 32 | 0.031 | | |

TABLE 4

Checkerboard assay of voriconazole and Mycograb (RTM) antibody against *Aspergillus* species

| Strain | Agent | MIC-2 (μg/ml) of each agent | | FIC (μg/ml) | FICI | Outcome |
|---|---|---|---|---|---|---|
| | | Alone | Combination | | | |
| *A. fumigatus* | VOR | 0.0625 | 0.0312 | 0.5 | 0.5 | Synergy |
| | Mycograb | 1024 | 0.25 | 0.0002 | | |
| *A. fumigatus* C12 | VOR | 0.25 | 0.125 | 0.5 | 0.5 | Synergy |
| | Mycograb | 1024 | 0.25 | 0.0002 | | |
| *A. niger* | VOR | 0.125 | 0.125 | 1 | 2 | Indifferent |
| | Mycograb | 16 | 16 | 1 | | |
| *A. flavus* | VOR | 0.25 | 0.0625 | 0.25 | 0.25 | Synergy |
| | Mycograb | 512 | 0.25 | 0.0005 | | |
| *A. terreus* | VOR | 0.25 | 0.125 | 0.5 | 0.5 | Synergy |
| | Mycograb | 1024 | 0.25 | 0.0002 | | |

SUMMARY

The results shown in Tables 1-4 reveal that while Mycograb® antibody on its own was able to inhibit growth of certain *Aspergillus* species, a surprisingly high level of antifungal activity against all the species examined was observed when the antibody was used in combination with itraconazole, and a surprisingly high level of antifungal activity against all the species examined except for *A. niger* was observed when the antibody was used in combination with voriconazole. This surprising effect between the antibody and itraconazole/voriconazole is not observed with other oral azole antifungal agents such as fluconazole, or with amphotericin B or caspofungin when combined with the antibody.

CONCLUSIONS

The data presented here clearly demonstrates that there is a surprising synergism between Mycograb® antibody and the antifungal agents itraconazole and voriconazole, which effects enhanced antifungal activity against a wide variety of pathologically important *Aspergillus* strains. These results allow for the use of compositions comprising either itraconazole and voriconazole, together with Mycograb® antibody for the treatment of human or animal fungal infections. The present invention allows for either lower treatment dosages or more effective treatment at the same dosages, thereby reducing unwanted side-effects.

There are several important clinical implications of the present invention. Firstly, the production of a synergistic combination of itraconazole/voriconazole and Mycograb® antibody in the treatment of *Aspergillus* infections should become the treatment of choice. This would lead to a reduction in mortality and morbidity for these infections. Secondly, itraconazole/voriconazole are associated with undesirable side effects in subjects receiving the drug. For example, voriconazole is very commonly associated with fever, headache, abdominal pain, nausea, vomiting, diarrhea, peripheral oedema, skin rash, and visual disturbances. The synergy provided by the present invention means that a lower dose of either itraconazole/voriconazole could be used while maintaining efficacy and concomitantly reducing toxicity and adverse side effects. Thirdly, the toxicity sparing effect of Mycograb® antibody would allow the clinical efficacy of higher doses of itraconazole/voriconazole to be explored and further contribute to an improved clinical outcome.

The invention claimed is:

1. A composition comprising an antibody or an antigen binding fragment thereof specific for an epitope of hsp90 from an organism of the *Aspergillus* genus, and at least one antifungal agent selected from the group consisting of: itraconazole and voriconazole.

2. The composition according to claim 1, wherein said antibody or antigen binding fragment is labelled with a detectable label.

3. The composition according to claim 1, wherein said antibody or an antigen binding fragment thereof is specific for the epitope of the sequence of SEQ ID NO: 2.

4. The composition according to claim 1, wherein said antibody or an antigen binding fragment thereof is specific for the epitope of the sequence of SEQ ID NO: 1.

5. The composition according to claim 4, wherein said antibody comprises the sequence of SEQ ID NO: 3.

6. A method of treating a fungal infection of the human or animal body comprising administering to a human or animal body suffering from or at risk for a fungal infection a therapeutically effective quantity of the composition according to claim 1.

7. The method according to claim 6, wherein said composition is administered orally.

8. The method of claim 6, wherein said fungal infection is due to an organism of the *Aspergillus* genus.

9. The method of claim 6, wherein the fungal infection is resistant to said antifungal agent per se.

10. The method according to claim 6, wherein said antibody or antigen binding fragment is labelled with a detectable label.

11. A method of manufacturing a medicament for the treatment of fungal infections of the human or animal body, comprising combining an antibody or an antigen binding fragment thereof specific for an epitope of hsp90 from an organism of the *Aspergillus* genus, with at least one antifungal agent selected from the group consisting of: itraconazole and voriconazole.

12. A method of treating fungal infections in a human or animal body, said method comprising administering to said human or animal body:
   (a) an antibody or antigen binding fragment thereof specific for an epitope of hsp90 from an organism of the *Aspergillus* genus; and
   (b) itraconazole or voriconazole;
   in amounts sufficient to treat a fungal infection in the human or animal body, wherein (a) and (b) are administered simultaneously or sequentially.

13. The method according to claim 12, wherein said fungal infection is due to an organism of the *Aspergillus* genus.

14. The method according to claim 12, wherein the fungal infection is resistant to said antifungal agent per se.

15. The method according to claim 12, wherein said antibody or antigen binding fragment is labelled with a detectable label.

16. The method according to claim 12, wherein (a) and (b) are administered orally.

17. The method according to claim 12, wherein said antibody or an antigen binding fragment thereof is specific for the epitope of the sequence of SEQ. ID NO. 1.

18. The method according to claim 12, wherein said antibody or an antigen binding fragment thereof is specific for the epitope of the sequence of SEQ. ID NO. 2.

19. The method according to claim 12, wherein said antibody comprises the sequence of SEQ. ID NO. 3.

20. A method of treating a fungal infection of a human or animal comprising administering to a human or an animal in need thereof an effective amount of:
   (a) an antibody or antigen binding fragment thereof that binds the epitope displayed by the peptide set forth in SEQ ID NO:1; and
   (b) at least one antifungal agent selected from the group consisting of itraconazole and voriconazole,
   wherein (a) and (b) are administered simultaneously or sequentially.

21. The method of claim 20, wherein said antibody or antigen binding fragment and said at least one antifungal agent are administered simultaneously.

22. The method of claim 20, wherein said antibody or antigen binding fragment and said at least one antifungal agent are administered sequentially.

23. The method of claim 20, wherein said fungal infection is due to an organism of the *Aspergillus* genus.

24. A method of treating a fungal infection of a human or animal comprising administering to a human or an animal in need thereof an effective amount of:
   (a) an antibody or antigen binding fragment thereof that binds the epitope displayed by the peptide set forth in SEQ ID NO:1; and
   (b) at least one antifungal agent selected from the group consisting of caspofungin and posaconazole,
   wherein (a) and (b) are administered simultaneously or sequentially.

25. The method of claim 24, wherein said antibody or antigen binding fragment and said at least one antifungal agent are administered simultaneously.

26. The method of claim 24, wherein said antibody or antigen binding fragment and said at least one antifungal agent are administered sequentially.

27. The method of claim 24, wherein said fungal infection is due to an organism of the *Aspergillus* genus.

* * * * *